United States Patent [19]

Nishiyama et al.

[11] 4,140,520
[45] Feb. 20, 1979

[54] 3,5-DICHLOROPYRIDYL-2-OXY-PHENOXY MALONIC ACIDS AND DERIVATIVES AND HERBICIDAL USE THEREOF

[75] Inventors: Ryuzo Nishiyama, Takatsuki; Kanichi Fujikawa, Kyoto; Isao Yokomichi, Kusatsu; Rikuo Nasu, Kusatsu; Nobuyuki Sakashita, Kusatsu, all of Japan

[73] Assignee: Ishihara Sangyo Kaisha Ltd., Oshaka, Japan

[21] Appl. No.: 785,817

[22] Filed: Apr. 8, 1977

[30] Foreign Application Priority Data

Apr. 8, 1976 [JP] Japan .................. 51-38708

[51] Int. Cl.$^2$ ............... A01N 9/22; C07D 213/64
[52] U.S. Cl. ........................... 71/94; 71/108; 71/116; 260/501.16; 560/62; 562/472; 546/302
[58] Field of Search ............ 71/94; 260/535 P, 295 R, 260/295 S

[56] References Cited

U.S. PATENT DOCUMENTS 3,954,422  5/1976  Becker et al. .............. 71/108
4,046,553  9/1977  Takahashi et al. .............. 71/94

FOREIGN PATENT DOCUMENTS 2531643  1/1976  Fed. Rep. of Germany.
2546251  4/1976  Fed. Rep. of Germany.

Primary Examiner—Richard Raymond
Attorney, Agent, or Firm—Sughrue, Rothwell, Mion, Zinn and Macpeak

[57] ABSTRACT

Phenoxy malonic acids and derivatives thereof represented by the general formula (I):

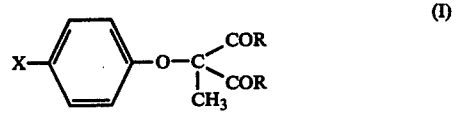

wherein X is a 4-trifluoromethylphenoxy group or a 3,5-dichloropyridyl-2-oxy group; and R is a hydroxy group, an —O— cation group or a ($C_1$ - $C_4$)alkoxy group, useful as a herbicide; a herbicidal composition containing the compound; and methods of controlling weeds using such materials.

6 Claims, No Drawings

3,5-DICHLOROPYRIDYL-2-OXY-PHENOXY MALONIC ACIDS AND DERIVATIVES AND HERBICIDAL USE THEREOF

BACKGROUND OF THE INVENTION

1. Field of the Invention

This invention relates to a compound useful as a herbicide for agriculture and horticulture, to a herbicidal composition containing the same, and to methods of controlling weeds.

2. Description of the Prior Art

Hitherto, various herbicides have been developed and practically used for contributing to a saving of man power and increasing the yields of agricultural products, but there is much room for improvement in such herbicides and the development of new and useful herbicides has been strongly desired. It is, of course, desirable to develop, for example, herbicides which are safe from the standpoint of environmental pollution and which have the least adverse effect on useful plants, still retaining strong herbicidal activities, but in view of the fact that the resistance of weeds to existing herbicides has increased recently, the demand for herbicides which have higher activity and are different types from existing herbicides has increased.

SUMMARY OF THE INVENTION

One object of the present invention is to provide phenoxy malonic acids and derivatives thereof which have advantageous herbicidal properties.

A further object of the present invention is to provide an effective herbicidal composition.

Still a further object of the invention is to provide a method for controlling weeds.

Accordingly, this invention, in one embodiment, provides phenoxy malonic acids and derivatives thereof represented by the general formula (I):

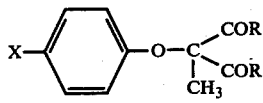

wherein X is a 4-trifluoromethylphenoxy group or a 3,5-dichloropyridyl-2-oxy group; and R is a hydroxy group, and —O— cation group or a ($C_1$ - $C_4$) alkoxy group.

In another embodiment, this invention provides a herbicidal composition comprising a herbicidally effective amount of at least one compound of the above general formula (I) and one or more agriculturally acceptable adjuvants.

In an even further embodiment of this invention, this invention provides a method of controlling weeds comprising applying a herbicidally effective amount of the above herbicidal composition to the weeds.

DETAILED DESCRIPTION OF THE INVENTION

In the definitions with respect to the formula (I) representing the compound of this invention, the cation can be a salt forming atom such as sodium, potassium, magnesium, calcium, etc., or a salt forming residue such as an ammonium group, an organic amine, etc., and the alkyl moiety in the ($C_1$ - $C_4$) alkoxy group can be a methyl, ethyl, n-propyl, isopropyl, n-butyl, isobutyl, sec-butyl or tert-butyl group.

The compound of this invention of the formula (I) can be prepared by the following methods:

Method (A)

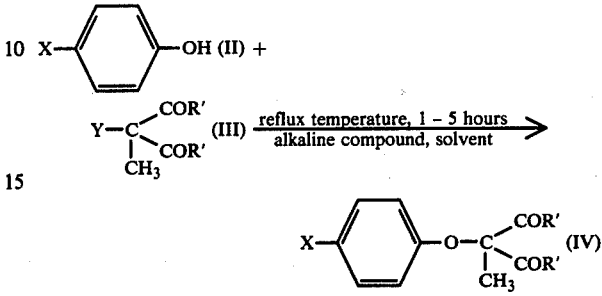

In the above reaction scheme, X is as defined above, R' is a ($C_1$ - $C_4$) alkoxy group, and Y is a chlorine or bromine atom.

Suitable examples of alkaline compounds used in the above reaction are sodium, potassium, sodium carbonate, potassium carbonate, etc., and suitable examples of solvents used in the above reaction are alcohols, ketones, dioxane, etc.

Method (B)

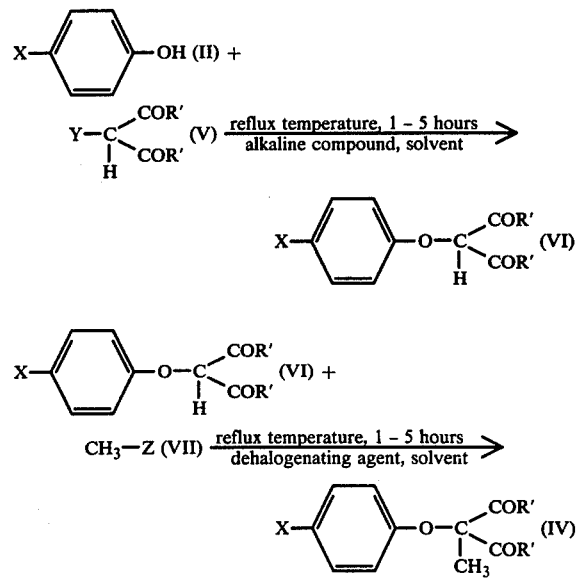

In the above reaction scheme, X, Y and R' are as defined above, and Z is a bromine or iodine atom.

Suitable examples of alkaline compounds and solvents for producing compound (VI) are the same as those used in Method (A). Suitable examples of dehalogenating agents which can be used are sodium amide, sodium ethoxide, etc., and suitable examples of solvents which can be used are alcohols, dioxane, etc.

The resulting compound of the formula (IV) is hydrolyzed to form a phenoxy malonic acid having the formula (VIII):

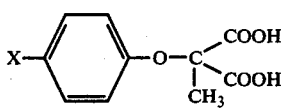

(VIII)

The phenoxy malonic acid having the formula (VIII) is further neutralized to form a salt.

The following Preparation Examples are given to illustrate the preparation of some typical compounds of this invention, but they are not to be construed as limiting the present invention. Unless otherwise indicated, all parts, percents, ratios and the like are by weight.

PREPARATION EXAMPLE 1

Preparation of α-[4-(4-Trifluoromethylphenoxy)phenoxy], α-Methyl Malonic Acid 3.6 g of α-[4-(4-trifluoromethylphenoxy)phenoxy], α-methyl malonic acid ethyl ester was dissolved in 20 ml of methanol, and an alkaline aqueous solution consisting of 2 ml of water and 0.7 g of sodium hydroxide was then dropwise added to the resulting mixture, followed by allowing the mixture to reflux for 1 hour. The reaction product was thrown into an appropriate amount of water to obtain crystals under acidic conditions with hydrochloric acid. The thus obtained crystals were filtered and recrystallized from acetic acid to obtain 3 g of the desired product having a melting point of 72° to 75° C.

PREPARATION EXAMPLE 2

Preparation of α-[4-(3,5-Dichloropyridyl-2-oxy)phenoxy], α-Methyl Malonic Acid Methyl Ester 5 g of 4-(3,5-dichloropyridyl-2-oxy)phenol was dissolved in 20 ml of methyl ethyl ketone, and 6.8 g of potassium carbonate was then added to the resulting mixture. To the mixture was further dropwise added 5.2 g of bromomethyl malonic acid methyl ester under heat-reflux conditions with stirring to allow the mixture to reflux for 2 hours. After filtering out inorganic salts which were formed, the solvent used was evaporated off from the reaction product. The thus obtained oily material was dissolved in an appropriate amount of benzene, followed by washing with a 5% sodium hydroxide aqueous solution. The benzene layer was dried over anhydrous sodium sulfate. The benzene was then evaporated off to obtain crude crystals. The crude crystals thus obtained were further recrystallized from methanol to obtain 6.5 g of the desired product having a decomposition point of 111° to 112° C. in the white crystalline form.

Typical compounds prepared by the above methods are listed below. Reference compound number designation set forth below will be made hereinafter in the specification.

Compound No. 1

α-[4-(4-Trifluoromethylphenoxy)phenoxy], α-Methyl Malonic Acid m.p. 72° - 75° C.

Compound No. 2

α-[4-(4-Trifluoromethylphenoxy)phenoxy], α-Methyl Malonic Acid Sodium Salt

Compound No. 3

α-[4-(4-Trifluoromethylphenoxy)phenoxy], α-Methyl Malonic Acid Ethyl Ester b.p. 188° - 194° C./4 mmHg

Compound No. 4

α-[4-(3,5-Dichloropyridyl-2-oxy)phenoxy], α-Methyl Malonic Acid 169° - 170° C. (decomposition)

Compound No. 5

α-[4-(3,5-Dichloropyridyl-2-oxy)phenoxy], α-Methyl Malonic Acid Sodium Salt

Compound No. 6

α-[4-(3,5-Dichloropyridyl-2-oxy)phenoxy], α-Methyl Malonic Acid Methyl Ester 111° - 112° C. (decomposition)

Compound No. 7

α-[4-(3,5-Dichloropyridyl-2-oxy)phenoxy], α-Methyl Malonic Acid Ethyl Ester 105° - 108° C. (decomposition)

Compound No. 8

α-[4-(3,5-Dichloropyridyl-2-oxy)phenoxy], α-Methyl Malonic Acid n-Propyl Ester

Herbicidal compositions containing the compounds of the present invention having the formula (I) above as active ingredients exhibit excellent herbicidal activities as shown in the Test Examples hereinafter described. In particular, it is noted that the compounds exhibit a peculiar selective herbicidal activity on gramineous weeds without causing any phytotoxic activity on crops such as cotton, soybeans, barley, wheat, etc. Thus, by taking advantage of such selective herbicidal activities of the compounds, the herbicidal compositions of this invention make it possible to control only noxious gramineous weeds which grow in crops cultivated on upland farms by applying the compositions in various application manners. Of course, the herbicidal compositions of the present invention can also be applied broadly to orchards, forests, various non-agricultural lands, paddy fields (low land fields) in addition to the upland farms by suitably selecting the application procedure, the amount of the composition to be used, etc. Also, such herbicidal compositions can be applied using various techniques such as soil treatment, foliar treatment and the like in a similar manner to conventional herbicidal compositions, as is well known in the art.

A suitable rate of application varies according to various factors such as the climatic conditions, the soil conditions, the form of the chemical, the time of application, the method of application, or the types of cultivated crops to which it is applied and the main weeds to be controlled. Usually the amount of the active ingredient is about 0.1 to about 1,000 g per are (100 m²), preferably 1 to 500 g per are, and more preferably 5 to 100 g per are. Especially, the amount of the active ingredient used on upland farms where barley or wheat is cultivated is 3 to 10 g per are.

The compound of this invention can be dispersed in water to produce an aqueous dispersion.

The compound of this invention can also be formulated into various forms such as an emulsifiable concentrate, a wettable powder, a water-miscible solution, a dust or granules by optionally incorporating conventional agriculturally acceptable adjuvants, for example, a carrier such as diatomaceous earth, calcium hydroxide, calcium carbonate, talc, white carbon, kaolin, bentonite or Jeeklite (trade name for kaolinite, produced by Jeeklite Co.), a solvent such as n-hexane, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium ligninsulfonate, a polyoxyethylene lauryl ether, a polyoxyethylene alkylaryl ether, a polyoxyethylene fatty acid ester or a polyoxyethylene sorbitan fatty acid ester. A suitable ratio of the compound of this invention to the adjuvant(s) ranges from about 1 to 90:99 to 10 by weight, preferably 1 to 70:99 to 30 by weight.

The herbicidal composition of this invention can also be mixed or used together with suitable agricultural chemicals such as other herbicides, insecticides or fungicides, or mixed with an agricultural agent such as a fertilizer or soil conditioner or soil or sand, at the time of formulation or application. Sometimes, such joint usage brings about improved effects.

Typical examples of herbicidal formulations containing a compound of this invention are shown below.

FORMULATION EXAMPLE 1

| (1) | α-[4-(3,5-Dichloropyridyl-2-oxy)phenoxy], α-Methyl Malonic Acid | 20 wt. parts |
|---|---|---|
| (2) | Xylene | 60 wt. parts |
| (3) | Sorpol 2806B | 20 wt. parts |
| | (trade name for a mixture of a polyoxyethylene phenyl phenol derivative, a polyoxyethylene alkylaryl ether, a polyoxyethylene sorbitan alkylate and an alkylaryl sulfonate produced by Toho Chemical Co., Ltd.) | |

The components (1) to (3) were uniformly mixed to form an emulsifiable concentrate.

FORMULATION EXAMPLE 2

| (1) | Jeeklite | 78 wt. parts |
|---|---|---|
| (2) | White Carbons | 15 wt. parts |
| (3) | Lavelin S | 2 wt. parts |
| | (trade name for a sodium naphthalene sulfonate-formaldhyde condensate produced by Daiichi Kogyo Seiyaku Co., Ltd.) | |
| (4) | Sorpol 5039 | 5 wt. parts |
| | (trade name for a sulfate of polyoxyethylene alkylaryl ether produced by Toho Chemical Co., Ltd.) | |

Components (1) to (4) were mixed and the mixture obtained was then mixed with α-[4-(4-trifluoromethylphenoxy)phenoxy], α-methyl malonic acid in a ratio of 4:1 by weight to form a wettable powder.

FORMULATION EXAMPLE 3

| (1) | α-[4-(3,5-Dichloropyridyl-2-oxy)phenoxy], α-Methyl Malonic Acid Methyl Ester | 7 wt. parts |
|---|---|---|
| (2) | Bentonite | 58 wt. parts |
| (3) | Jeeklite | 30 wt. parts |
| (4) | Sodium Ligninsulfonate | 5 wt. parts |

Components (1) to (4) were mixed. A little amount of water was added to the resulting mixture. Then, they were granulated to form granules.

The herbicidal activity of the compound of this invention was tested as shown below and the results obtained are also shown below.

TEST EXAMPLE 1

Each 1/3,000 are (1/30 m$^2$) flat was charged with soil to provide upland farm conditions. Predetermined amounts of seeds of edible barnyard grass, radish and soybeans were sown and covered with soil containing seeds of large crabgrass (*Digitaria adscendens* HENR.), green foxtail (*Setaria viridis* BEAUV.) and barnyard grass (*Echinochloa crus-galli* BEAUV.) as gramineous weeds to a thickness of about 1 cm. Three days after sowing, an aqueous dispersion of each of the compounds shown in Table 1 was sprayed thereon, and the growth of the weeds and crops was visually evaluated 20 days after the spraying. The results obtained are shown in Table 1. The degree of growth inhibition shown in Table 1 was evaluated on a scale of 10 grades in which 10 indicates that growth was completely inhibited and 1 indicates no inhibition.

TABLE 1

| Compound No. | Amount of Active Ingredient (g/are) | Edible Barnyard Grass | Radish | Soybeans | Gramineous Weeds |
|---|---|---|---|---|---|
| 1 | 100 | 10 | 1 | 1 | 10 |
|   | 50 | 10 | 1 | 1 | 10 |
| 2 | 100 | 10 | 1 | 1 | 10 |
|   | 50 | 9 | 1 | 1 | 10 |
| 3 | 100 | 10 | 1 | 1 | 10 |
|   | 50 | 9 | 1 | 1 | 10 |
| 4 | 100 | 10 | 1 | 1 | 10 |
|   | 50 | 10 | 1 | 1 | 10 |
| 5 | 100 | 10 | 1 | 1 | 10 |
|   | 50 | 10 | 1 | 1 | 10 |
| 6 | 100 | 10 | 1 | 1 | 10 |
|   | 50 | 10 | 1 | 1 | 10 |
| 7 | 100 | 10 | 1 | 1 | 10 |
|   | 50 | 10 | 1 | 1 | 10 |
| 8 | 100 | 10 | 1 | 1 | 10 |
|   | 50 | 10 | 1 | 1 | 10 |

TEST EXAMPLE 2

Each 1/10,000 are (1/100 m$^2$) pot was charged with soil to provide upland farm conditions. Predetermined amounts of seeds of edible barnyard grass, radish and soybeans were sown and covered with soil to a thickness of about 1 cm. When the edible barnyard grass reached a two-leaf stage, an aqueous dispersion of each of the compounds shown in Table 2 was applied to foliage in a predetermined amount. Twenty days after treatment with the dispersion, the growth of weeds and crops was visually evaluated, and the degree of growth inhibition was evaluated on the same scale as in Text Example 1. The results obtained are shown in Table 2.

TABLE 2

| Compound No. | Concentration of Active Ingredient (ppm) | Edible Barnyard Grass | Radish | Soybeans |
|---|---|---|---|---|
| 1 | 2,000 | 10 | 1 | 1 |
|   | 1,000 | 10 | 1 | 1 |
| 3 | 2,000 | 10 | 1 | 1 |
|   | 1,000 | 9 | 1 | 1 |
| 4 | 2,000 | 10 | 1 | 1 |
|   | 1,000 | 10 | 1 | 1 |
| 5 | 2,000 | 10 | 1 | 1 |
|   | 1,000 | 10 | 1 | 1 |
| 6 | 2,000 | 10 | 1 | 1 |
|   | 1,000 | 7 | 1 | 1 |
| 7 | 2,000 | 10 | 1 | 1 |
|   | 1,000 | 10 | 1 | 1 |

TEST EXAMPLE 3

Each 1/10,000 are (1/100 m²) pot was charged with soil and completely saturated with water. A predetermined amount of air-dried seeds of barnyard grass was sown and lightly covered with soil. When the barnyard grass germinated above the ground, water was put into the pot to a depth of 3 cm to provide flooded conditions, and an aqueous dispersion of each of the compounds shown in Table 3 was poured into the pot. Fourteen days after treatment with the dispersion, the surviving barnyard grass in the pot was pulled out, dried in air, and weighed. The percentage of the amount of surviving weeds based on the untreated pot was calculated, and the degree of growth determined (with 0% meaning no growth and 100% no inhibition). The results obtained are shown in Table 3.

| Compound No. | Degree of Growth (%) Amount of Active Ingredient (g/are) | |
|---|---|---|
|  | 40 | 20 |
| 1 | 0 | 0 |
| 3 | 0 | 0 |
| 4 | 0 | 0 |
| 5 | 0 | 0 |
| 6 | 0 | 0 |
| 7 | 0 | 0 |
| 8 | 0 | 0 |

TEST EXAMPLE 4

Each 1/5,000 are (1/50 m²) pot was charged with soil to provide upland farm conditions. Predetermined amounts of seeds of wheat, barley and wild oat were sown and covered with soil to a thickness of about 1 cm. When the wild oat and crops reached a three-leaf stage, an aqueous dispersion of each of the compounds shown in Table 4 was applied to foliage in a predetermined amount. Forty days after treatment with the dispersion, the growth of weeds and crops was visually evaluated, and the degree of growth inhibition was evaluated on the same scale as in Test Example 1. The results obtained are shown in Table 4.

TABLE 4

| Compound No. | Amount of Active Ingredient (g/are) | Degree of Growth Inhibition | | |
|---|---|---|---|---|
|  |  | Crops | | Weeds |
|  |  | Wheat | Barley | Wild Oat |
| 1 | 2 | 1 | 1 | 4 |
|  | 4 | 1 | 1 | 6 |
|  | 6 | 1 | 2 | 7 |
|  | 8 | 2 | 3 | 9 |
| 3 | 2 | 1 | 1 | 4 |
|  | 4 | 1 | 1 | 7 |
|  | 6 | 2 | 3 | 7 |
|  | 8 | 2 | 3 | 9 |
| 4 | 2 | 1 | 1 | 7 |
|  | 4 | 1 | 1 | 10 |
|  | 6 | 2 | 2 | 10 |
|  | 8 | 4 | 4 | 10 |
| 6 | 2 | 1 | 1 | 7 |
|  | 4 | 1 | 2 | 10 |
|  | 6 | 2 | 2 | 10 |
|  | 8 | 4 | 4 | 10 |
| Ethyl-α-[4-(4-trifluoromethyl-phenoxy)phenoxy]propionate | 2 | 8 | 9 | 9 |
|  | 4 | 10 | 10 | 10 |
|  | 6 | 10 | 10 | 10 |
|  | 8 | 10 | 10 | 10 |
| Sodium-α-[4-(3,5-dichloropyridyl-2-oxy)phenoxy]-propionate | 2 | 10 | 10 | 10 |
|  | 4 | 10 | 10 | 10 |
|  | 6 | 10 | 10 | 10 |
|  | 8 | 10 | 10 | 10 |

TEST EXAMPLE 5

Each 1/5,000 are (1/50 m²) pot was charged with soil to provide upland farm conditions. Predetermined amounts of seeds of crops (soybeans and cotton) were sown and covered with soil to a thickness of about 1 cm. When the crops reached a two-leaf stage, an aqueous dispersion of each of the compounds shown in Table 5 was applied to foliage in a predetermined amount. Twenty-five days after treatment with the dispersion, the growth of crops was visually evaluated and the degree of growth inhibition (degree of phytotoxicity) was evaluated on the same scale as in Test Example 1. The results obtained are shown in Table 5.

TABLE 5

| Compound No. | Amount of Active Ingredient (g/are) | Degree of Growth Inhibition (Phytotoxicity) | |
|---|---|---|---|
|  |  | Soybeans | Cotton |
| 1 | 7.5 | 1 | 1 |
|  | 15 | 1 | 1 |
|  | 20 | 1 | 2 |
| 3 | 7.5 | 1 | 1 |
|  | 15 | 1 | 1 |
|  | 20 | 1 | 2 |
| 4 | 7.5 | 1 | 1 |
|  | 15 | 1 | 1 |
|  | 20 | 1 | 1 |
| 6 | 7.5 | 1 | 1 |
|  | 15 | 1 | 1 |
|  | 20 | 1 | 1 |
| Methyl-α-[4-(2,4-dichlorophenoxy)-phenoxy]-propionate | 7.5 | 4 | 4 |
|  | 15 | 4 | 6 |
|  | 20 | 6 | 8 |

While the invention has been described in detail and with reference to specific embodiments thereof, it will be apparent to one skilled in the art that various changes and modifications can be made therein without departing from the spirit and scope thereof.

What is claimed is:

1. A compound having the general formula

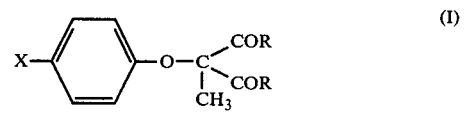

wherein X is a 3,5-dichloropyridyl-2-oxy group; and R is a hydroxy group, an —O—cation group in which the cation is herbicidally acceptable or a ($C_1$ - $C_4$) alkoxy group.

2. The compound of claim 1 wherein the compound is α-[4-(3,5-dichloropyridyl-2-oxy)phenoxy],α-methyl malonic acid.

3. The compound of claim 1, wherein the compound is α-[4-(3,5-dichloropyridyl-2-oxy)phenoxy],α-methyl malonic acid sodium salt.

4. The compound of claim 1, wherein the compound is α-[4-(3,5-dichloropyridyl-2-oxy)phenoxy],α-methyl malonic acid methyl ester.

5. A herbicidal composition comprising a herbicidally effective amount of at least one compound having the general formula (I):

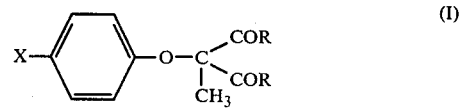

wherein X is a 3,5-dichloropyridyl-2-oxy group; and R is a hydroxy group, a —O—cation group in which the cation is herbicidally acceptable or a ($C_1$–$C_4$) alkoxy group as an active ingredient and an agriculturally acceptable adjuvant.

6. A method for controlling noxious weeds in the presence of cultivated crops which comprises applying a herbicidally effective amount of a herbicidal composition of claim 5.

* * * * *